United States Patent [19]

Mark, Jr.

[11] Patent Number: 4,644,336

[45] Date of Patent: Feb. 17, 1987

[54] COLOR DISPLAY OF RELATED PARAMETERS

[75] Inventor: Richard H. Mark, Jr., Pitcairn, Pa.

[73] Assignee: Westinghouse Electric Corp., Pittsburgh, Pa.

[21] Appl. No.: 621,003

[22] Filed: Jun. 15, 1984

[51] Int. Cl.$^4$ ............................................. A09A 1/28
[52] U.S. Cl. ................................... 340/701; 324/220; 340/721
[58] Field of Search ............... 340/701, 703, 721, 722, 340/709, 715, 743; 324/220, 221, 222

[56] References Cited

U.S. PATENT DOCUMENTS

| | | | |
|---|---|---|---|
| 3,434,158 | 3/1969 | Stauffer et al. | 340/722 X |
| 3,596,284 | 7/1971 | Zaphiropoulos | 346/46 X |
| 3,895,290 | 7/1975 | Audenard et al. | 324/233 |
| 4,026,144 | 5/1977 | Gericke et al. | 358/82 X |
| 4,188,577 | 2/1980 | Mhatre et al. | 324/220 |
| 4,194,149 | 3/1980 | Holt et al. | 324/220 |
| 4,210,917 | 7/1980 | Lane, III | 346/46 X |
| 4,480,225 | 10/1984 | Nance et al. | 324/220 X |

Primary Examiner—Marshall M. Curtis
Assistant Examiner—Vincent P. Kovalick
Attorney, Agent, or Firm—Daniel C. Abeles

[57] ABSTRACT

A method and apparatus for producing a color strip display of eddy current test data from a signal produced by an eddy current detector and which varies in amplitude and in phase relative to a reference signal as the detector is displaced relative to a test body. In order to produce the display, a signal representative of the relative displacement of the detector, a signal representative of the amplitude of the detector signal, and a signal representative of the relative phase of the detector signal are produced and the representative signals are supplied to a color display device for producing a strip display which extends along a path determined by the signal representative of the relative displacement of the detector, has an amplitude perpendicular to the path which is a function of the signal representative of the amplitude of the detector signal, and has a color the hue of which is a function of the signal representative of the relative phase of the detector signal.

12 Claims, 4 Drawing Figures

COLOR DISPLAY OF RELATED PARAMETERS

BACKGROUND OF THE INVENTION

The present invention relates to a method and an apparatus for producing displays of several related but independently variable parameters of an occurrence.

The invention is particularly applicable to the evaluation of test data produced by an eddy current detector and which contains information relative to the position of the detector relative to the body of the detector, the amplitude of the detector output signal, and phase shifts between that output signal and a phase reference. Such testing is performed, for example, to detect flaws, such as cracks, in steam generator tubes.

Known eddy current detectors include two coils mounted in adjacent arms of a bridge. An alternating current is passed through the bridge to generate an electromagnetic field. This field will be influenced by an adjacent metal body to vary the impedance of one or both coils, thereby creating an unbalance voltage in the bridge, which voltage is the difference between the voltages across the two coils. Thus, the waveform of the unbalance voltage is constituted by a carrier wave at the alternating current frequency modulated by the difference between the impedance variations in the two coils.

FIG. 1 illustrates the voltages induced across the two coils of an eddy current detector when moving past a flaw in the body being tested. The respective voltage curves 25 and 26 are offset in time because they are spaced apart in the direction of movement of the eddy current detector. The curves shown represent the modulation of the carrier wave, or waves, which are not represented in FIG. 1. Therefore, the phase variations ocurring in the carrier wave, or waves, are not represented.

The duration of each curve 25, 26 depends on the length of the flaw in the direction of detector movement while the peak amplitude of each curve depends on the extent of the flaw. The carrier wave shift in the coil voltage is a function of the nature, and particularly the depth, of the faw.

FIG. 2 shows curve 28 representing the resulting bridge unbalance voltage which is the difference between curves 25 and 26 of FIG. 1.

Heretofore, evaluation of eddy current test data has involved generation of a strip chart constituted by the waveform of the bridge unbalance voltage amplitude, as the ordinate, with respect to displacement of the eddy current detector along a surface of the metal body being tested, as the abscissa.

Such evaluation further includes analysis of the phase displacement between the applied alternating current and the unbalance bridge voltage for a section of the strip chart in which the waveform has an unusual configuration. This can be achieved by obtaining representations of the unbalance voltage components which are in phase with and in quadrature, or 90° out of phase, with the alternating current applied to the bridge.

Then a Lissajous figure representing a plot of the in-phase amplitude vs. the quadrature phase amplitude can be generated to permit more detailed analysis of the defect which produced the associated waveform segment. For example, a Lissajous figure permits determination of the depth of a crack or of the type of defect. However, a Lissajoua figure does not contain any information relating to detector position along the test body surface. This general technique is described, for example, in U.S. Pat. No. 3,895,290.

Thus, the above-described procedure requires two independent displays, neither of which contains all available information relating to detector position, unbalance voltage amplitude and unbalance voltage phase.

It is also known to generate two strip charts each depicting the amplitude of a respective unbalance voltage component relative to detector position. In this case, phase information is still not present in a readily observable form.

SUMMARY OF THE INVENTION

It is an object of the invention to produce displays which simultaneously present information representing three related but independently variable parameters.

A more specific object of the invention is to generate a display which simultaneously depicts in a readily discernable manner three parameters of an eddy current detector signal.

The above and other objects are achieved, according to the invention, by a method for producing a color strip display of eddy current test data from a signal produced by an eddy current detector and which varies in amplitude and in phase relative to a reference signal as the detector is displaced relative to a test body, comprising: producing a signal representative of the relative displacement of the detector, a signal representative of the amplitude of the detector signal, and a signal representative of the relative phase of the detector signal; and supplying the representative signals to a color display device for producing a strip display which extends along a path determined by the signal representative of the relative displacement of the detector, has an amplitude perpendicular to the path which is a function of the signal representative of the amplitude of the detector signal, and has a color the hue of which is a function of the signal representative of the relative phase of the detector signal.

More generally, the objects of the invention are achieved by a method for producing a color strip display containing information relating to three related but independently variable parameters, comprising: producing signals representing successive values of each parameter with respect to a common time scale; applying the signals associated with a first one of the parameters to a color display device for producing a strip display which extends along a path corresponding to the first parameter with successive points along the path corresponding to successive values of the first parameter; applying the signals associated with a second one of the parameters to the color display device for causing the amplitude of the strip display perpendicular to the path to be a function of successive values of the second parameter at successive points along the path; and applying the signals associated with the third one of the parameters to the color display device for causing the hue of the strip display to be a function of successive values of the third parameter at successive points along the path.

Objects of the invention are further achieved by the provision of apparatus for producing a color strip display of eddy current test data from a signal produced by an eddy current detector and which varies in amplitude and in phase relative to a reference signal as the detector is displaced relative to a test body, comprising: means for producing a signal representative of the relative displacement of the detector, a signal representative of the amplitude of the detector signal, and a signal representative of the relative phase of the detector signal; and means for supplying the representative signals to a color display device for producing a strip display which extends along a path determined by the signal representative of the relative displacement of the detector, has an amplitude perpendicular to the path which is a function of the signal representative of the amplitude of the detector signal, and has a color the hue of which is a function of the signal representative of the relative phase of the detector signal.

Objects of the invention are additionally achieved by the provision of apparatus for producing a color strip display containing information relating to three related but independently variable parameters, comprising: means for producing signals representing successive values of each parameter with respect to a common time scale; means for applying the signals associated with a first one of the parameters to a color display device for producing a strip display which extends along a path corresponding to the first parameter with successive points along the path corresponding to successive values of the first parameter; means for applying the signals associated with a second one of the parameters to the color display device for causing the amplitude of the strip display perpendicular to the path to be a function of successive values of the second parameter at successive points along the path; and means for applying the signals associated with the third one of the parameters to the color display device for causing the hue of the strip display to be a function of successive values of the third parameter at successive points along the path.

DESCRIPTION OF THE PREFERRED EMBODIMENTS

Figure 1:
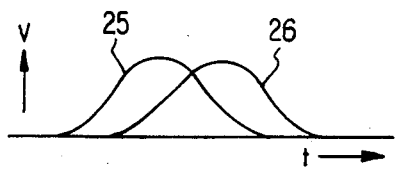
FIGS. 1 and 2 are waveform diagrams which have already been described.

When performing eddy current testing, the alternating current applied to the bridge of an eddy current detector may be a sinusoidal current at a single frequency or may contain several frequencies. By way of example, the alternating current may be composed of sinusoidal waves having frequencies, f, of 400 kHz, 100 kHz and 10 kHz so that the bridge unbalance voltage will be composed of three signals each a modulated version of the carrier wave at a respective one of these frequencies. Each frequency is useful for examining flaws at a different depth in the body being tested. Therefore, a procedure utilizing several different frequencies offers certain advantages.

For each carrier frequency, f, the corresponding unbalance voltage signal will be divided into a component $Ex_f$ which is in phase with the associated carrier frequency, f, and a component $Ey_f$ which is in quadrature with the associated carrier frequency, f.

In addition, to eliminate unwanted signals, it can be useful to derive inphase and quadrature components based on a mixture of the components associated with several carrier frequencies. For example, the following component signals have been found to be useful for observing certain types of flaws:

$$Ex_{mix} = a \cdot Ex_{400} + b \cdot Ex_{100} + c \cdot Ey_{400} + d \cdot Ey_{100};$$

$$Ey_{mix} = e \cdot Ey_{400} + f \cdot Ey_{100} + g \cdot Ex_{400} + h \cdot Ex_{100};$$

where $Ex_{400}$ and $Ex_{100}$ are the in-phase components of the 400 kHz and 100 kHz unbalance voltage signals, $Ey_{400}$ and $Ey_{100}$ are the quadrature components of the 400 kHz and 100 kHz unbalance voltage signals, etc. The coefficients a–h are derived statistically, according to the principles known in the art, under consideration of the particular body, the types of flaws to be observed, and the signals to be eliminated.

A display according to the invention can be in the form of a waveform which extends along an axis and which contains information identifying three related parameters. If the waveform axis corresponds to the length of a steam generator tube being tested, each point along the axis of the waveform corresponds to a location along the length of the tube. Thus, the location of a waveform point along the axis constitutes a first parameter.

The amplitude of the waveform at each point along the axis corresponds to the amplitude of the eddy current detector unbalance voltage signal associated with the corresponding point along the length of the tube and constitutes the second signal parameter.

The color of the waveform at each point along the axis corresponds to the phase shift experienced by the unbalance voltage signal when the detector is at the corresponding point along the tube length and constitutes the third signal parameter.

A display according to the invention will be derived from the value pairs: $Ex_{400}$, $Ey_{400}$; or $Ex_{100}$, $Ey_{100}$; or $Ex_{10}$, $Ey_{10}$; or $Ex_{mix}$, $Ey_{mix}$. Four displays can be produced simultaneously each based on a respective value pair. When each display extends along a linear axis representing the reference for the first parameter, the four displays can be produced adjacent one another with their first parameters in mutual registry.

However, in contrast to the prior art in which display information is derived from the amplitudes of the unbalance voltage components, the signal values for a display according to the invention are based on the rate of change of the unbalance voltage components.

Figure 2:
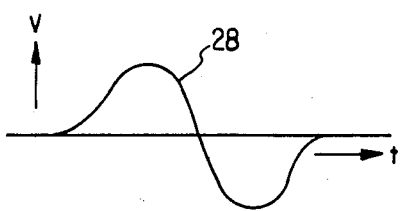
Figure 3:
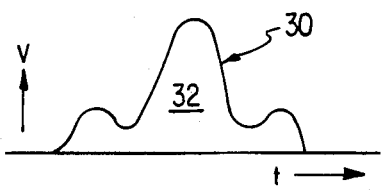
FIG. 3 is a waveform diagram illustrating a novel principle of displays according to the invention.

FIG. 3 shows a curve 30 which represents the absolute value of the rate of change, or first time derivative, of curve 28 of FIG. 2. Curve 30 is an approximation of, and corresponds conceptually to, the envelope of a display according to the invention with respect to a flaw which produced unbalance voltage curve 28. In a display according to the invention, the region 32 between the peak portion of curve 30 and the waveform base line, or axis, will be filled with a color field the hue of which corresponds to the depth of the associated flaw.

Utilization of rate-of change values offers the advantage of eliminating data falsifications which could result from voltage fluctuations. For example, even if curve 28 of FIG. 2 should shift relative to its voltage reference level, this would not affect the corresponding rate-of change values.

Figure 4:
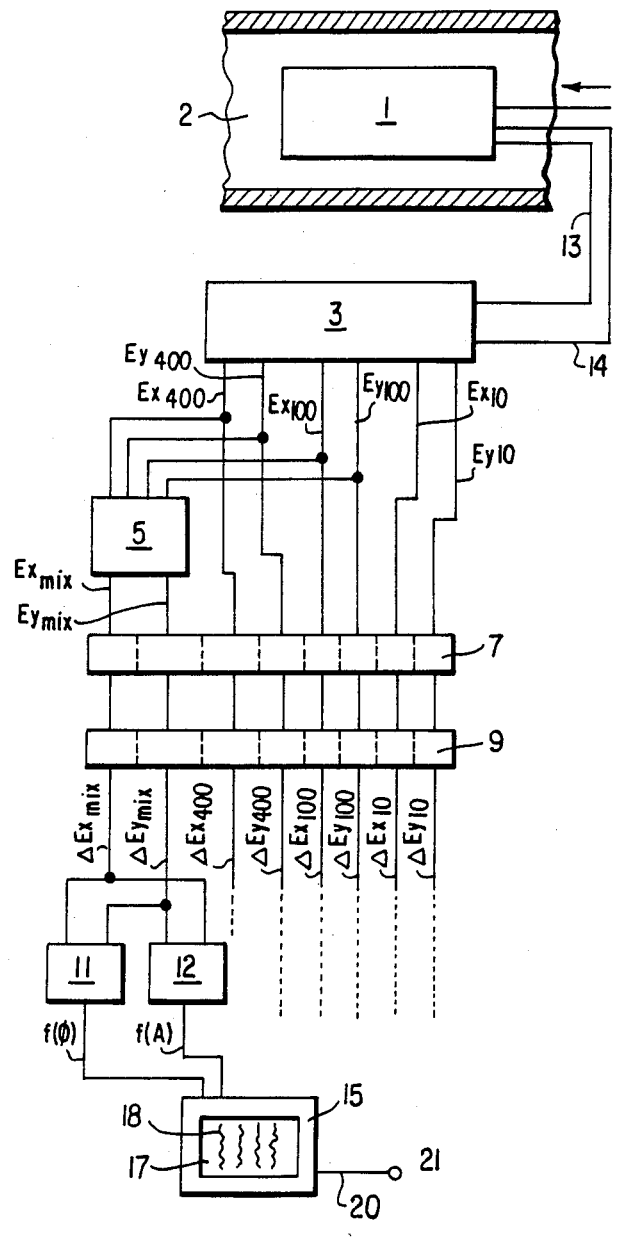
FIG. 4 is a block circuit diagram of apparatus for implementing the invention.

One embodiment of a system for implementing the invention is shown in FIG. 4. An eddy current detector 1, which can be constructed according to conventional practice and which includes two coils connected in a bridge circuit, is mounted to be introduced into a tube 2 to be tested, and to be displaced along the tube axis. The supply of operating power to detector 1 is not shown.

Signals are conducted from detector 1 to a signal processing circuit 3 via conductors 13 and 14. One of these conductors carries the bridge unbalance voltage signal and the other conductor carries a signal corresponding to the alternating current and constituting the phase reference for deriving in-phase and quadrature components of the bridge unbalance voltage signal associated with each alternating current frequency.

In circuit 3, which can be constructed according to known principles, the unbalance voltage signals are separated according to carrier frequency and each signal is then divided, for example, by correlation or mixing, into its $E_x$ and $E_y$ components, as shown at the outputs of circuit 3.

The components associated with the frequencies of 400 and 100 kHz are conducted to a combining circuit 5, also constructed according to known principles, in which the components $Ex_{mix}$ and $Ey_{mix}$ are formed.

All Ex and Ey components are conducted to a sampling circuit 7 which samples each component at a sufficiently high rate to preserve the information contained therein and then supplies the successive sample values of each component to a difference circuit 9 where the difference between successive sample values of each component is generated. The broken lines in block 7 and 9 indicate that each component remains in a separate signal processing channel. Circuits 7 and 9 can be constructed according to known principles.

The successive difference values, $\Delta Ex$ and $\Delta Ey$, derived for each component pair are supplied to a respective phase function circuit 11 and amplitude function circuit 12. Only the function circuits associated with $\Delta Ex_{mix}$ and $\Delta Ey_{mix}$ are shown, for ease of understanding. In the complete system, similar function circuits will be provided for each component pair.

Circuit 11 generates successive signal values which are a function of $\phi = \arctan(\Delta Ey_{mix}/\Delta Ex_{mix})$ for each pair of difference signals appearing simultaneously at the outputs of circuit 9. These signal values are supplied to a color control input of a color graphics display unit 15 having a screen 17 to control the hue of an associated trace 18 constituting the waveform associated with $Ey_{mix}$ and $Ex_{mix}$.

The signal produced by circuit 11 is selected to vary the color content of the display in the region of each peak of the associated trace over a range extending, for example, from yellow-green through yellow and orange to red, the yellow-green end of the range corresponding to a minimum value of phase and, for example, a crack depth of less than 20% of the tube wall thickness, the red end corresponding to a maximum value of $\phi$ and, for example, a crack extending completely through the tube wall. In general, $\phi$ will vary as a function of the depth of a flaw, such as a crack.

Circuit 12 generates signal values which are a function of the amplitude of the mixture signal. Specifically, the signal values produced by circuit 12 are proportional to $|\sqrt{(\alpha Ex_{mix})^2 + (\Delta Ey_{mix})Hu\, 2}|$. These signal values are supplied to a deflection input of unit 15 to control the horizontal deflection of the trace in a single direction from its axis, or base line. In general, the amplitude value produced by circuit 12 will be representative of the extent of a flaw, such as a crack.

In the illustrated arrangement, the axis, or base line, of each trace 18 is vertical and each point along the axis corresponds to a respective position of detector 1 along the axis of tube 2. In order to control the vertical deflection of each trace 18, i.e., its displacement along the vertical axis, unit 15 is provided with a suitable vertical deflection signal via a conductor 20 connected to an input contact 21. This signal is correlated with the displacement of detector 1.

Circuits 11 and 12 perform relatively simple functions and could be constructed according to known principles.

Unit 15 could also be of the type having only one color control input and one horizontal deflection input. In this case, as is well known, each circuit 11 and each circuit 12, there being four of each in the complete system, could be connected to a multiplexer which supplies a signal value from each circuit in turn to the associated terminal input. An incremental horizontal deflection voltage would be added to each successive amplitude signal to associate the resulting deflection signal with its corresponding trace.

In the resulting display, each trace 18 will have, at each point along its axis, an amplitude representative of the rate of change of the associated unbalance voltage signal, or the corresponding rate of change of the mixture signal, and each peak region of the trace will have a color whose hue is representative of the ratio of the incremental change in the quadrature component to the incremental change in the in-phase component of the unbalance voltage signal.

Since the trace extends along an axis correlated with the position of detector 1 along the axis of tube 2, trace 18 will additionally provide information as to the location, length and type of flaw being detected.

Normally, the test data values produced by circuits 11 and 12 will be recorded for study at a later time. For this purpose, the successive values of $f(\phi)$ and $f(\Delta)$ can be recorded in digital form. One system which has been used to produce a display according to the invention from such recorded signals was composed of a Data General MV Series Computer, a Data General Dasher D 200 terminal including an operating keyboard and monitor and a Raster Technologies Model 120 or 125 color graphics display system. A suitable program for producing a display according to the invention, consisting of four parallel traces, appears at the end of the specification. This program is written in Fortran 77.

The display is generated so that the waveform produced by the amplitude signal forms an envelope which is filled in with the appropriate color, i.e., a color field extends from the amplitude curve to the base line. This facilitates observation of the color information.

The display according to the invention can also be generated in the form of a color print-out.

It will be understood that the above description of the present invention is susceptible to various modifications, changes and adaptations, and the same are intended to be comprehended within the meaning and range of equivalents of the appended claims.

```
      SUBROUTINE COLOR_STRIP_CHART(NP1,NP2)
      COMMON/SCREEN_POS/IC,NCOLPS,NCOLPS2,NCOLPS3,NCOLPS1
      COMMON/DATA_POS/NSTEP,NP,NST(5),IST,NMAX,IDIR
      COMMON/DATA/IDATA,ICL
      DIMENSION XMAX(4)
      DIMENSION IANGL(4)
      INTEGER*2 IDATA(8,51200)
      CHARACTER*1 ANS
      DIMENSION ICO(4,512),XHI(4,512),IAN(4,512)
      CALL MENU_COLOR
      DO 8 I=1,4
3     XMAX(I)=0.
      NPT=NP
      N2=460
      IF(NPT/NSTEP.LT.N2)N2=NPT/NSTEP
      NTOP=NPT
      CALL WRMASK(191,4)
      CALL LUTRTE(125)
      CALL VAL3(0)
      CALL CLEAR
      CALL QUIT
      DO 2 IL=1,N2
      DO 3 II=1,4
      I1=II*2-1
      I2=II*2
      IX1=IDATA(I1,NPT)
      IX2=IDATA(I1,NPT+1)
      IY1=IDATA(I2,NPT)
      IY2=IDATA(I2,NPT+1)
      DELTAX=(IX2-IX1)
      DELTAY=(IY2-IY1)
      CALL GET_POLAR(DELTAX,DELTAY,XHI(II,IL),ANGLE)
      IANG=ANGLE+.5
      IF(XHI(II,IL).EQ.0.)THEN
            ICOL=0
      ELSE
            ICOL=(MOD(IANG+360,360)*50)/360
      ENDIF
      IAN(II,IL)=IANG
      ICO(II,IL)=ICOL+13
3     CONTINUE
      DO 5 J=2,NSTEP
      DO 5 II=1,4
      I1=II*2-1
      I2=II*2
      IX1=IDATA(I1,NPT+J-1)
      IX2=IDATA(I1,NPT+J)
      IY1=IDATA(I2,NPT+J-1)
      IY2=IDATA(I2,NPT+J)
      DELTAX=(IX2-IX1)*1633.3
      DELTAY=(IY2-IY1)*1633.3
      CALL GET_POLAR(DELTAX,DELTAY,XHIGH,ANGLE)
      IANG=ANGLE+.5
      IF(XHIGH.EQ.0.)THEN
            ICOLOR=0
      ELSE
            ICOL=(MOD(IANG+360,360)*50)/360
            ICOLOR=ICOL+13
      ENDIF
      IF(XHIGH.GT.XHI(II,IL))THEN
            XHI(II,IL)=XHIGH
            ICO(II,IL)=ICOLOR
            IAN(II,IL)=IANG
      ENDIF
5     CONTINUE
      IF(NP1.LE.NPT.AND.NP2.GE.NPT)THEN
            DO 7 I=1,4
7           XMAX(I)=AMAX1(XHI(I,IL),XMAX(I))
      ENDIF
      NPT=NPT-NSTEP
2     CONTINUE
      NPT=NTOP
      CALL ENTGRA
      CALL STRIP_SUB_COLOR(ICO,XHI,XMAX,4,N2,NPT)
      CALL VAL3(T28)
      CALL MOVREL(0,(NP1-NPT)/NSTEP)
      CALL DRWREL(512,0)
      CALL MOVREL(0,(NP2-NP1)/NSTEP)
```

```
         CALL DRWREL(-512,0)
         CALL WRMASK(123,4)
19       CALL READBUT(1,1,IBUT,IX,IY)
         IF(IBUT.EQ.1)THEN
                 JP=220-IY
                 IPOS=NPT-(219-IY)*NSTEP
                 CALL VAL3(0)
                 CALL CLEAR
                 CALL VAL8(123)
                 CALL MOVABS(-256,IY)
                 CALL DRWREL(512,0)
                 CALL QUIT
                 PRINT*,'ANGLES IN DEGREES AT POSITION ',IPOS
                 PRINT*,'400,100,10,MIX ',(MOD(IAN(I,JP)+360,360),I=1,4)
                 CALL ENTGRA
                 GO TO 19
         ELSE IF(IBUT.EQ.2)THEN
                 JP1=220-IY
                 CALL VAL3(0)
                 CALL CLEAR
                 CALL VAL3(123)
                 CALL MOVABS(-256,IY)
                 CALL DRWREL(512,0)
                 CALL READBUT(1,1,IBUT,IX,IY)
                 JP2=220-IY
                 CALL MOVABS(-256,IY)
                 CALL DRWREL(512,0)
                 CALL QUIT
                 IF(JP1.GT.JP2)THEN
                         JP=JP1
                         JP1=JP2
                         JP2=JP
                 ENDIF
                 IPOS1=NPT-(1+JP1)*NSTEP
                 IPOS2=NPT-(1+JP2)*NSTEP
                 PRINT*,'AVERAGE ANGLES IN DEGREES BETWEEN ',IPOS1,
            &           ' AND ',IPOS2
                 DO 17 I=1,4
17               IANGL(I)=MOD(IAN(I,JP1)+360,360)
                 DO 18 JP=JP1+1,JP2
                 DO 18 I=1,4
18               IANGL(I)=IANGL(I)+MOD(IAN(I,JP)+360,360)
                 NJ=1+JP2-JP1
                 PRINT*,'400,100,10,MIX ',(IANGL(I)/NJ,I=1,4)
                 CALL ENTGRA
                 GO TO 19
         ELSE IF(IBUT.EQ.12)THEN
                 CALL QUIT
                 PRINT*,'DO YOU WANT TO QUIT [Y] '
                 READ(5,'(A)')ANS
                 IF(ANS.NE.'N'.AND.ANS.NE.'n')STOP
                 CALL ENTGRA
                 GO TO 19
         ELSE IF(IBUT.NE.13)THEN
                 GO TO 19
         ENDIF
         CALL MOVABS(-256,219)
         CALL MENU_LISS
         RETURN
         END
         SUBROUTINE STRIP_SUB_COLOR(ICO,XHI,XMX,N1,N2,NPT)
         COMMON/DATA_POS/NSTEP,NP,NST(5),IST,NMAX,IDIR
         CHARACTER*5 CPOS
         DIMENSION ICO(N1,N2),XHI(N1,N2),XMX(N1)
         XMXT=0.
         DO 4 I=1,4
         XMXT=AMAX1(XMX(I),XMXT)
4        CONTINUE
         DO 5 I=1,4
         IF(XMX(I).LT.XMXT/10.)XMX(I)=XMXT
5        CONTINUE
         CALL MOVABS(-256,219)
         CALL RNBHDR(N2,512)
         DO 2 JJ=1,N2
         NPP=NPT-NSTEP*(JJ-1)
         IC3=0
         IF(MOD(NPP+10,10).EQ.0)THEN
```

```
              IF(MOD(NPP+50,50).EQ.0)THEN
                     IF(MOD(NPP+100,100).EQ.0)THEN
                              ICB=11
                     ELSE
                              IF(NSTEP.LT.10)ICB=10
                     ENDIF
              ELSE
                     IF(NSTEP.LT.2)ICB=9
              ENDIF
       ENDIF
       DO 1 I=1,4
       IXHI=MAX(0,MIN(122,1+INT(120*XHI(I,JJ)/XMX(I))))
       ION=IXHI+5
       IOFF=128-ION
       IF(ION.GT.0)CALL RN8STR(MAX(0,MIN(255,ICO(I,JJ))),ION)
       IF(IOFF.GT.0)CALL RN8STR(ICB,IOFF)
   1   CONTINUE
   2   CONTINUE
       ICC=51200
       CALL VAL8(12)
       DO 3 JJ=1,N2
       NPP=NPI-NSTEP*(JJ-1)
       INUM=NPP-4*NSTEP
       IF(MOD(INUM+200,200).EQ.0)THEN
              IF(MOD(INUM+1000,1000).EQ.0.OR.NSTEP.LT.20)THEN
                     CALL CMOVE(22,0)
                     IY=MOD(986+ICC,512)-256
                     WRITE(CPOS,'(I5.5)')INUM
                     CALL MOVABS(-253,IY)
                     CALL TEXT1(5,CPOS)
                     IF(IY.GT.240)THEN
                            CALL MOVREL(0,-512)
                            CALL TEXT1(5,CPOS)
                     ENDIF
                     CALL CMOVE(0,22)
              ENDIF
       ENDIF
       ICC=ICC-1
   3   CONTINUE
       RETURN
       END
       SUBROUTINE COLOR_STRIP_SET(TITLE,N)
       CHARACTER*(*) TITLE(N)
       NCOLPS=512/N
       NCOLPS1=NCOLPS-1
       NCOLPS2=NCOLPS/2
       NCOLPS3=NCOLPS-3
       CALL WRMASK(255,4)
       CALL PRMFIL(0)
       CALL VAL8(54)
C                           OUTLINE EACH CHART
       CALL MOVABS(-256,-255)
       DO 8 I=1,N
       CALL DRWREL(0,476)
       CALL MOVREL(NCOLPS1,0)
       CALL DRWREL(0,-476)
       CALL MOVREL(1,0)
C                           END OF OUTLINE
       CALL MOVABS(-256,-255)
       CALL RECTAN(255,-240)
       CALL MOVREL(36,5)
       CALL TEXT1(10,TITLE(1))
       DO 2 I=2,N
       CALL MOVREL(NCOLPS,0)
       CALL TEXT1(10,TITLE(I))
       CALL MOVABS(-256,220)
       CALL RECTAN(255,255)
       CALL MOVREL(36,4)
       CALL TEXT1(10,TITLE(1))
       DO 3 I=2,8
       CALL MOVREL(NCOLPS,0)
       CALL TEXT1(10,TITLE(I))
       CALL MOVABS(-156,242)
       CALL CRIGHT
       CALL MOVABS(-253,226)
       CALL AILOGO
       RETURN
       END
```

```
SUBROUTINE GET_POLAR(X,Y,R,T)
R=SQRT(X**2+Y**2)
IF(X.EQ.0.)THEN
                IF(Y.GE.0.)THEN
                        T=90.
                ELSE
                        T=-90.
                ENDIF
ELSE
                IF(Y.EQ.0.)THEN
                        T=0.
                ELSE
                        T=180.*ATAN2(Y,X)/3.141592653
                ENDIF
ENDIF
RETURN
END
SUBROUTINE MENU_COLOR
CALL QUIT
WRITE(6,100)
100     FORMAT('1',T20,'TABLET FUNCTIONS FOR COLOR PATTERNS '//
      & '   BUTTON     FUNCTION'//
      & '   GRAY       RETURN TO LISSAJOUS             '/
      & '    1         DETERMINE ANGLE AT A LOCATION   '/
      & '    2         DETERMINE AVERAGE ANGLE BETWEEN 2 LOCATIONS '/
      & '    3         NO FUNCTION                     '/
      & '    4         NO FUNCTION                     '/
      & '    5         NO FUNCTION                     '/
      & '    6         NO FUNCTION                     '/
      & '    7         NO FUNCTION                     '/
      & '    8         NO FUNCTION                     '/
      & '    9         NO FUNCTION                     '/
      & '    0         NO FUNCTION                     '/
      & '    *         NO FUNCTION                     '/
      & '    #         QUIT')
CALL ENTGRA
RETURN
END
```

I claim:

1. A method for producing a color display of eddy current test data from a signal produced by an eddy current detector and which varies in amplitude and in phase relative to a reference signal as the detector is displaced relative to a test body, comprising:
producing a signal representative of the relative displacement of the detector, a signal representative of the amplitude of the detector signal, and a signal representative of the relative phase of the detector signal; and
supplying the representative signals to a color display device for producing a trace which varies with respect to a base line, wherein the trace passes through a line that is perpendicular to the base line at a point on the base line that is determined by the signal representative of the relative displacement of the detector, wherein the trace has an amplitude, along the line perpendicular to the base line, that is a function of the signal representative of the amplitude of the detector signal, and wherein at least one colored point is displayed along the line that is perpendicular to the base line, the at least one colored point having a hue that is a function of the signal representative of the relative phase of the detector signal.

2. A method as defined in claim 1 wherein the at least one colored point is a colored region extending from the base line to the trace.

3. A method as defined in claim 1 wherein the signal representative of the amplitude of the detector signal is proportional to the rate of change of that amplitude.

4. A method as defined in claim 1 wherein the signal produced by the detector has a component which is in quadrature with the reference signal and a component which is in phase with the reference signal, and wherein the signal representative of the relative phase of the detector signal is proportional to an angle whose tangent is the ratio between two values, one of the values being the incremental chane in the amplitude of the component of the detector signal which is in quadrature with the reference signal and the other of the values being the incremental change in the amplitude of the component of the detector signal which is in phase with the reference signal.

5. A method as defined in claim 1 wherein the amplitude of the trace contains a peak value representing each flaw encountered by the detector, and the at least one colored point includes a color region enclosed by each amplitude peak and having a hue representative of the depth of the associated flaw.

6. A method as defined in claim 5 wherein the color region extends from the base line to the trace for all points on the trace.

7. A method as defined in claim 1 wherein the detector produces a plurality of signals each associated with a reference signal having a respectively different frequency, and said steps of producing a signal and supplying the representative signals are carried out to produce a plurality of traces and respective base lines, each trace and respective base line being based on a respective detector signal.

8. A method as defined in claim 2 wherein the traces are disposed side-by-side with their respective base lines parallel to one another.

9. A method as defined in claim 1 wherein the trace produced by the color display device is in printed form.

10. A method for producing a color display containing information relating to three related but independently variable parameters, comprising:
producing signals representing successive values of each parameter with respect to a common time scale;
applying the signals associated with a first one of the parameters to a color display device for producing a trace which varies with respect to a base line, with successive points along the base line corresponding to successive values of the first parameter;
applying the signals associated with a second one of the parameters to the color display device for causing the amplitude of the trace perpendicular to the base line to be a function of successive values of the second parameter at successive points along the base line; and
applying the signals associated with the third one of the parameters to the color display device for causing the device to display a succession of sets of at least one colored point, each set corresponding to a respective successive point along the base line, the hue of the colored points of the sets being a function of successive values of the third parameter at successive points along the path.

11. Apparatus for producing a color display of eddy current test data from a signal produced by an eddy current detector and which varies in amplitude and in phase relative to a reference signal as the detector is displaced relative to a test body, comprising:
means for producing a signal representative of the relative displacement of the detector, a signal representative of the amplitude of the detector signal, and a signal representative of the relative phase of the detector signal; and
means responsive to the representative signals for producing a trace which varies with respect to a base line, the trace passing through a line that is perpendicular to the base line at a point on the base line that is determined by the signal representative of the relative displacement of the detector, the trace having an amplitude, along the line perpendicular to the base line, that is a function of the signal representative of the amplitude of the detector signal, the means for producing a trace additionally including means for displaying at least one colored point along the line that is perpendicular to the base line, the at least one colored point having a hue that is a function of the signal representative of the relative phase of the detector signal.

12. Apparatus for producing a color display containing information relating to three related but independently variable parameters, comprising:
first means for producing signals representing successive values of each parameter with respect to a common time scale; and
second means electrically connected to the first means for visually depicting information derived from the signals, the second means including
means responsive to the signals associated with a first one of the parameters for producing a trace which varies with respect to a base line, with successive points along the base line corresponding to successive values of the first parameter,
means responsive to the signals associated with a second one of the parameters for causing the amplitude of the trace perpendicular to the base line to be a function of successive values of the second parameter at successive points along the path, and
means responsive to the signals associated with the third one of the parameters for causing a succession of sets of at least one colored point to be displayed, each set corresponding to a successive point along the base line, the hue of the colored points of the sets being a function of successive values of the third parameter at successive points along the path.

* * * * *